United States Patent [19]
O'Connell et al.

[11] Patent Number: 5,772,983
[45] Date of Patent: Jun. 30, 1998

[54] METHODS OF SCREENING FOR COMPOUNDS WHICH MODULATE INSECT BEHAVIOR

[75] Inventors: Robert J. O'Connell, Worcester; Alan J. Grant, Watertown, both of Mass.

[73] Assignee: Worcester Foundation For Biomedical Research, Shrewsbury, Mass.

[21] Appl. No.: 543,271

[22] Filed: Oct. 16, 1995

[51] Int. Cl.$^6$ .......................... A61K 49/00; G01N 31/00; G01N 33/48
[52] U.S. Cl. .................................................. 424/9.2
[58] Field of Search .................................. 424/1.11, 9.1, 424/9.2, 900; 43/112; 119/6.5

[56] References Cited

PUBLICATIONS

Hildebrand (1995), Proc. Natl. Acad. Sci., USA, vol. 92, pp. 67–74 "Analysis of Chemical Signals by Nervous Systems", Jan. 3, 1995.
Galun (1977) *Entomol. Soc. Am.* 257–265.
Steinbrecht (1984) *Biology of the Integument*, Springer–Verlag, Berlin, vol. 1, Ch. 28, pp. 523–553.
Daykin et al. (1965) *Canadian Entomol.* 97:239–263.
Takken (1991) *Insect Sci. Applic.* 12:287–295.
Otter et al. (1988) *Insect Sci. Applic.* 9:213–318.
Acree et al. (1968) *Science* 161:1346–1347.
Smith et al. (1969) *Ann. Entomol. Soc. Am.* 63:760–768.
Gillies (1980) *Bull. Ent. Res.* 70:525–532.
Mayer et al. (1969) *Bull. Ent. Res.* 58:628–641.
Kline et al. (1990) *Med. Veter. Entomol.* 4:383–391.
Kline et al. (1991) *J. Med. Entomol.* 28:254–258.
Roth (1951) *Ann. Entomol. Soc. Am.* 44:59–74.
Jones et al. (1976) *Ent. Exp. Appn,* 19:19–22.
Bowen (1991) *Ann. Rev. Entomol.* 36:139–158.
Davis (1977) *J. Insect Physiol.* 23:613–617.
Davis (1985) *J. Med. Entomol.* 22:237–243.
Davis (1976) *J. Comp. Physiol. A* 105:43–54.
McIver (1971) *Can. J. Zool.* 49:235–239.
Borroni et al. (1979) *J. Comp. Physiol. A* 170:691–700.
Kellog (1970) *J. Insect Physiol.* 16:99–108.
Galun (1977) *Entomol. Soc. Am.* 257–265.
McIver (1972) *Can. J. Zool.* 50:571–576.
Bogner (1990) *J. Insect. Physiol.* 36:951–957.
Stange et al. (1973) *J. Comp.Physiol.* 86:139–158.
Lacher (1964) *Z. verlag Physiol.* 48:587–623.
Bogner (1992) *Physiol. Entomol.* 17:19–24.
Bogner et al. (1986) *J. Comp. Physiol.* 158:741–749.
Steullet et al. (1992) *J. Comp. Physiol.* 170:665–676.
Grant et al. (1995) *J. Comp. Physiol.* A177:389–396.
Steinbrecht (1984) *Springer–Verlag*, Berlin pp. 523–553.
O'Connell (1975) *J. Gen. Physiol.* 65:179–205.
Otter et al. (1988) Insect Sci. Applic. 9:213–318.

*Primary Examiner*—John Kight
*Assistant Examiner*—Dameron L. Jones
*Attorney, Agent, or Firm*—Lappin & Kusmer LLP

[57] ABSTRACT

Disclosed is a method of selecting for a compound which modulates the behavior of an insect. In this method, electrical characteristics of an insect chemoreceptor neuron in the presence of control stimulation, then a known chemical modulator of insect activity, and then a test compound are measured after the neuron is contacted therewith. These measurements are compared and the test compound classified based on this comparison.

40 Claims, 6 Drawing Sheets

CONTROL

FIG. 5A

CITRONELLAL
0.0001 μg

FIG. 5B

1-OCTEN-3-OL
0.0001 μg

METHODS OF SCREENING FOR COMPOUNDS WHICH MODULATE INSECT BEHAVIOR

FUNDING

Work described herein was supported in part by NIH grant No. DC 000131 from NIDCD.

FIELD OF THE INVENTION

This invention relates to the control of insect behavior. More particularly, this invention pertains to methods of screening for chemical compounds which modulate insect behavior by exploiting sensory capabilities of the target insect.

BACKGROUND OF THE INVENTION

Each year there are over 300 million clinical cases involving at least five major diseases that are transmitted by insects. Over 1.5 million fatalities annually can be attributed to mosquito-transmitted diseases alone, or to their complications (*Malaria: Obstacles and Opportunities: A Report of the Committee for the Study on Malaria Prevention and Control*, Washington, D.C., National Academy Press (1991) pp. 1–309; WHO Malaria Unit (1993) *Bull. World Health Org.* 71:281–284; and WHO Malaria Unit (1993) *Weekly Epidemiol. Rec.* 68:253–260). For decades, efforts have been made to better understand the mechanisms that underlie host attraction, feeding, and mating of hematophagous insects (see, e.g., Friend et al. (1977) *Ann. Rev. Entomol.* 22:309–331; Galun (1977) *Entomol. Soc. Am.* 257–265.

For example, attempts have been made to describe and synthesize the complex interactions which underlie host-seeking behavior in mosquitoes (Daykin et al. (1965) *Can. Ent.* 97:239–263; Takken (1991) *Sci. Applic.* 12:287–295). Factors including moisture and heat (Clements in *The Physiology of Mosquitoes*, (1963) Pergamonn Press, Oxford, pp. 128–150; Christopher in *Aedes Aegypti (L.) The Yellow Fever Mosquito* (1960) Cambridge University Press, Cambridge pp. 530–547), host volatiles such as lactic acid (Acree et al. (1968) *Science* 161:1346–1347; Smith et al. (1969) *Ann. Entomol. Soc. Am.* 63:760–768), carbon dioxide (Gillies (1980) *Bull. Ent. Res.* 70:525–532; Mayer et al. (1969) *Bull. Ent. Res.* 58:628–641); and other volatiles (Kline et al. (1990) *Med. Veter. Entomol.* 4:383–391; Kline et al. (1991) *J. Med. Entomol.* 28:254–258) appear to be important stimuli for mosquito orientation. The ability to alter or eliminate the orientation and feeding behaviors guided by these stimuli has enormous potential for the control of mosquito-born diseases, and have a positive impact on world health (*Malaria: Obstacles and Opportunities: A Report of the Committee for the Study on Malaria Prevention and Control*, Washington, D.C. National Academy Press (1991) pp. 1–309).

It is known that chemoreceptor neurons on various parts of an insect including the maxillary palps and antennae play an important role in the detection and processing of the chemical stimuli that have been implicated in initiating and modulating host-seeking and other behaviors (see, e.g., Roth (1951) *Ann. Entomol. Soc. Am.* 44:59–74; Jones et al. (1976) *Ent. Exp. Appn.* 19:19–22; Gillies (1980) *Bull. Ent. Res.* 70:525–532; Kline et al. (1991) *J. Med. Entomol.* 28:254–258). However, physiological studies of the peripheral sensory system in mosquitoes have focused largely on the responses of olfactory receptor neurons in antennal sensilla. Although antenna sensilla in mosquitoes do contain a highly sensitive lactic acid receptor neuron whose activity can be modulated by the behavioral repellent DEET (Bowen (1991) *Ann. Rev. Entomol.* 36:139–158; Davis (1977) *J. Insect Physiol.* 23:613–617; Davis (1985) *J. Med. Entomol.* 22:237–243; Davis (1976) *J. Comp. Physiol. A* 105:43–54), additional specialized, high sensitivity receptors tuned to the other behaviorally relevant compounds have not been found on this sensory appendage. Chemoreceptors for other synthetic and natural compounds do exist in mosquito antennal sensilla, but they generally require relatively large unphysiological doses to elicit electrophysiological responses, suggesting that they do not play a large role in providing the sensory inputs required for orientation behavior. Little additional information is available which bears directly on the sensory mechanisms involved with the detection and processing of volatile stimuli by receptor neurons in host-seeking insects. It has been suggested, however, that the number, distribution, and specificity, of particular chemoreceptors on the antennal and palpal sense organs in various species of mosquito are related to differences in the insects' relative preferences for hosts (McIver (1971) *Can. J. Zool.* 49:235–239; Braverman et al. (1979) *J. Med. Entomol.* 15:419–424). Therefore, a physiological study of the other chemoreceptors in several species should reveal important clues about the chemical stimuli which initiate and modulate host-seeking behavior.

There are three primary receptor neurons in sensilla basiconica on the maxillary palps of mosquitoes and two or more in similar sensilla of other insects. The neurons in a single sensillum represent a set of sensory inputs which share a common extracellular environment, cuticular structure, and spatial location. One of the neurons in the labial palp basiconica sensillum in mosquitoes is responsive to carbon dioxide (Kellogg (1970) *J. Insect Physiol.* 16:99–108). Carbon dioxide has long been implicated as an important chemical signal utilized by mosquitoes and other hematophagous insects in their host-seeking and feeding behaviors (Bowen (1991) *Ann. Rev. Entomol.* 36:139–158; Galun (1977) *Entomol. Soc. Am.* 257–265). Receptor neurons which respond to carbon dioxide have been identified and studied morphologically in mosquitoes (McIver (1972) *Can. J. Zool.* 50:571–576), and physiologically in several other arthropods including Lepidoptera (Bogner (1990) *J. Insect Physiol.* 36:951–957; Bogner et al. (1986) *J. Comp. Physiol.* 158:741–749), Hymenoptera (Stange et al. (1973) *J. Comp. Physiol.* 86:139–158; Lacher (1964) *Z. verlag Physiol.* 48:587–623), other Diptera (Bogner (1992) *Physiol. Entomol.* 17:19–24), and Arachnida (Steullet et al. (1992) *J. Comp. Physiol. A.* 170:665–676). In the mosquito sensilla basiconica, this carbon dioxide-sensitive neuron has response properties that are likely appropriate for orientation behavior (Grant et al. (1995) *J. Comp. Physiol. A* 177:389–396).

Knowledge of the stimuli and response properties of other specific olfactory receptor neurons, such as the other two primary neurons in the sensilla basiconica, was heretofore lacking. Such knowledge can provide the framework within which to evaluate chemical compounds as potential insect control agents. This knowledge in turn leads to the design of much needed and improved bio-rational methods of insect control.

Thus, what is needed are methods of screening for compounds which modulate insect behavior. Such methods should exploit the sensory capabilities of the target insect and lead to control measures which are cost effective and amenable to relatively simple trap designs.

SUMMARY OF THE INVENTION

The present invention provides screening methods for identifying compound which modulate insect behavior by exploiting the sensory capabilities of the target insect. These control methods are cost effective, amenable to relatively simple trap designs, and ultimately increase the overall degree of protection of the world's population against insect borne diseases.

It is known that insect chemosensory sensilla often contain two or more developmentally related chemoreceptor neurons (Steinbrecht (1984) *Springer-Verlag, Berlin* pp. 523–553), each of which produces typical biphasic action potentials of various sizes and shapes in extracellular recordings (O'Connell (1975) *J. Gen. Physiol.* 65:179–205). In the case of the mosquito, sensilla basiconica on the maxillary palps contain three neurons. One of these, neuron A, produces a large amplitude action potential and responds to carbon dioxide (Kellogg (1970) *J. Insect Physiol.* 16:99–108). The other two, neurons B and C, produce smaller amplitude action potentials in response to stimuli other than carbon dioxide. It has been discovered that neuron C in certain mosquito sensilla basiconica respond electrophysiologically to very small amounts of known modulators of insect behavior other than carbon dioxide. This discovery has been exploited to produce the present invention which provides, in one aspect, a method of identifying compounds which modulate the behavior of an insect.

In accordance with the method of the invention, an electrical characteristic of a chemoreceptor neuron in a sensillum of the insect sought to be controlled is measured in the presence of various stimuli to determine a measure of the activity for the neuron.

For purposes of the invention, the term "electrical characteristic" is meant to encompass all types of discernible electrical properties or attributes exhibited by the chemoreceptor neuron under a variety of conditions. An electrical characteristic of a neuron includes the electrical activity generated by the neuron in response to an applied stimulus. The electrical activity may be expressed in a number of representative forms such as potential difference, current, impedance measurements, electric field, and capacitance. In many cases, the electrical characteristic will be in the form of potential difference and particularly will be a variable frequency succession of voltage pulses, referred to as action potentials.

The term "sensillum" encompasses a cuticular structure or sense organ which houses chemoreceptor neuron(s) and which is found on the surface of an insect. In preferred embodiments, the neurons contacted are within a multiporous sensillum such as a sensillum basiconicum, sensillum trichodea, sensillum coeloconicum, or sensilla ampullacea. In other embodiments, the neuron contacted is a multiporous sensillum on an insect from the Diptera, Lepidoptera, Coleoptera, Hymenoptera, Siphonaptera, or Orthoptera orders. In some embodiments of the invention, the chemoreceptor neurons are carbon dioxide-insensitive, such as neurons B and C in the sensilla basiconica of the mosquito labial palps. The term "carbon dioxide-insensitive chemoreceptor neuron" refers to chemoreceptor neurons which are not stimulated by, or which do not respond electrophysiologically to, carbon dioxide in the range of 150 to 4000 ppm.

The term "control stimulation" as used herein refers to contact of the neuron under test with a substance that does not stimulate the receptor neuron, such as air or a diluent. "Baseline activity" is used herein to mean the native activity of the neuron without chemical stimulation. In a subsequent step, the neuron is contacted during a stimulation period with a known chemical modulator of insect behavior.

The term "known modulator of insect behavior" refers to compounds either singly or in combination which are known to cause the insect to act in a particular fashion, including materials that cause the insect to shun a host or mate, or to be attracted to a usually indifferent, unattractive or repulsive substance. The known modulator also stimulates a chemoreceptor neuron in a sensillum to respond. In some embodiments of the invention, the types of insect behavior sought to be modulated by the present method include host-seeking behavior and mate-seeking behavior.

In preferred embodiments of the invention, the contacting step includes directing a volatile form of the known compound or the compound being tested toward the sensillum. In some embodiments, the compound-to-be-tested is a single volatile material. In other embodiments, it is a multicomponent volatile material.

In the first or baseline step (a) of the method, the chemoreceptor neuron in a sensillum of the insect sought to be controlled is measured in the presence of a control stimulation to determine a baseline activity (A) for the neuron. In the calibration step (c) of the method, an electrical characteristic of the contacted neuron produced in response to the contacting with the known modulator (step (b)) is measured to provide a measure of known modulator-induced activity (C) for the neuron, wherein C is representative of a correlation between the neuron and the modulator-induced behavior of the insect.

In a test step (e), the same chemoreceptor neuron is contacted (in step (d)) with a compound-to-be-tested, and an electrical characteristic produced by the contacted neuron in response to the contacting with the compound is measured to determine a measure of unknown modulator-induced activity (E) of the neuron. The measures A, C, and E are then compared. When C is greater than A, the compound is classified with respect to its ability to modulate the behavior of the insect based on the comparison step.

In one preferred embodiment, the electrical characteristics measured are potential differences. As used herein, the term "potential difference" refers to an energy gradient defined as the difference in electrical field values between two points and expressed as a voltage amplitude. In this embodiment, each of the measuring steps includes the following. A recording electrode is inserted into the base of the sensillum such that it is in electrical contact with the electrical field of the neuron. A second electrode is inserted into an interior region of the insect external to or remote from the sensillum. The difference in electrical potential between the first and second electrodes is then measured.

In preferred embodiments, the measurement values A, C, and E of a first neuron in the sensillum and the measurement values A, C, and E of a second neuron in the sensillum are resolved such that A, C, and E of the first neuron are distinguishable from A, C, and E of the second, third, and/or other chemoreceptor neuron(s) in the sensillum. In one particular embodiment, the second and third chemoreceptor neurons are mosquito sensilla basiconica neurons B and C.

In preferred embodiments, the detected potential differences are in the form of a varying frequency succession of voltage pulses or action potentials, produced by the neuron. Each pulse succession may be characterized as having an average pulse repetition rate, and at each point in time, an instantaneous pulse repetition rate.

In one embodiment, A is representative of the number of pulses produced by the neuron in the baseline step (a) during a period corresponding to the stimulation period; C is the number of pulses produced by the neuron during the stimulation period in the calibration step (c); and E is the number of pulses produced by the neuron during a period corresponding to the stimulation period in the test step (e).

For purposes of the invention, the term "stimulation period" refers to the preset and limited time period during which the known modulator response of the neuron is measured in the calibration step. The term "a period corresponding to the stimulation period" refers to a comparable preset and limited time period during which the baseline and test responses of the neuron are measured in the baseline and test steps, respectively.

In other embodiments, A is representative of the peak instantaneous repetition rate of the pulses produced by the neuron in the baseline step during a period corresponding to the stimulation period; C is the peak instantaneous repetition rate of the pulses produced by the neuron in the calibration step during the stimulation period; and E is the peak instantaneous repetition rate of the number of pulses produced by the neuron in the test step during a period corresponding to the stimulation period. As used herein, "peak instantaneous repetition rate" refers to the maximum action potential pulse repetition rate during the measurement period.

In yet other embodiments, C is representative of the third moment of the distribution of interpulse periods of the succession of pulses produced by the neuron in the calibration step during the stimulation period, and E is representative of the third moment of the distribution of interpulse period of the secession of pulses produced by the neuron in the test step during a period corresponding to the stimulation period. C or E each are in a range from −1 to +1 on the real number line. In this embodiment, in order to define A, C, and E as metrics of neuron activity which "increase" with activity, a first value of C or E is greater than a second value of C or E, respectively, if the first value is closer to −1 on the real number line than is the second value. For purposes of the invention the "third moment of the distribution of interpulse periods of the succession of pulses" is used to mean a value proportional to A $$\frac{\sum_i (i - \bar{i})^2 Q_i}{\sum_i Q_i}$$

where i is the value of the $i^{th}$ interpulse spacing in the distribution, i is the average or mean interpulse spacing for the distribution, and $Q_i$ is the number of occurrences of the ith interpulse spacing. In general, the third moment is a measure of skewness of the distribution of interpulse periods, ranging from −1 to +1 in the real number line, and where, for the preferred embodiment, a value closer to −1 refers to a predominance of short interpulse periods (indicating relatively high activity), while a value closer to +1 refers to a predominance of long interpulse periods (indicating relatively low activity).

In another embodiment of the method of the invention, A is representative of the mean instantaneous pulse repetition rate during the baseline step. In addition, the succession of pulses produced by the neuron in the calibration step is characterized by an initial phasic component followed by a tonic component during the stimulation period. During the phasic component, a relatively large number of pulses per unit time are produced by the neuron and during the tonic component, a relatively small number of pulses are produced by the neuron per unit time. "$C_T$" is representative of the mean instantaneous pulse repetition rate during the tonic component, "$C_P$" is representative of the peak instantaneous pulse repetition rate during the phasic component, and $C_P^2/C_T$ corresponds to C. Furthermore, the succession of pulses produced by the neuron in the test step is characterized by an initial phasic component followed by a tonic component during a period corresponding to the stimulation period, wherein during the phasic component, a relatively large number of pulses per unit time are produced by the neuron and during the tonic component, a relatively small number of pulses are produced by the neuron per unit time. $E_T$ is representative of the mean instantaneous pulse repetition rate during the tonic component, $E_P$ is representative of the peak instantaneous pulse repetition rate during the phasic component, and $E_P^2/E_T$ corresponds to E. Other activity measurements, and ratios, may alternatively be used to provide a metric of activity of the neuron.

Following the determination of the values A, C, and E, those values are compared. When C is greater than A, indicating that for the measured electrical characteristic, the known modulator provides a detected value C indicating greater activity than the detected baseline value A, the various values A, C, and E are further compared and conclusions drawn as to the relative effect on modulation of the compound under test.

When E equals C, the compound is classified as having potency substantially equal to the known modulator. When E is greater than C, the compound is classified as having greater potency than the known modulator. When E is less than C, and E is greater than A, the compound is classified as having lesser potency than the known modulator. When E is less than A, the compound is classified as being an inhibitor of the behavior modulated by the known modulator.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

The present invention provides a method of screening for compounds which modulate insect behavior, thus effectuating bio-rational methods of insect survey and control. Knowing that a compound which modulates the behavior of an insect also causes a particular electrophysiological response in a chemoreceptor neuron enables the identification of other behaviorally relevant compounds which cause a similar electrophysiological response.

As used herein, the term "bio-rational" refers to methods of control which use "natural" components in a rational way. It is used in contrast to other methods which use "synthetic" compounds such as pesticides without regard to their impact on the rest of the ecosystem. The assumption here is that evolution has provided the insect with the olfactory receptors needed for the detection of those chemicals which naturally modulate their behavior. These receptors are used herein in a potent screening method to look for other compounds that are as good, better, or less expensive stimuli for these receptors.

An object of insect control is to modulate an insect behavior or activity to reduce the irritation, sickness, or death of a host, or to decrease the general health and proliferation of the insect. Such insect activities include host-seeking behavior and mate-seeking behavior. Host-seeking behavior encompasses locating a suitable host to obtain food and moisture (e.g., by biting animals, sampling secretions, or eating plant matter) and locating an appropriate surface or other venue on or in which to lay their eggs. Thus, by modulating normal insect behavior, e.g., by enticing an insect to a trap, to eat poison or other non-nutritional compounds which may result in their sterilization or by causing a host to become repulsive to the insect, insect disease proliferation can be controlled.

A range of compounds has been shown to modulate various aspects of mosquito behavior. TABLE 1 lists some representative behaviorally relevant compounds in mosquitoes.

TABLE 1

| Known Behavior Modulators | Responsive Insect Behavior |
|---|---|
| carbon dioxide | attractant |
| L(+) lactic Acid | attractant |
| DEET, N,N-diethyl-m-toluamide | repellant |
| 1-octen-3-ol | attractant |
| Jasmonate | repellant |

TABLE 1-continued

| Known Behavior Modulators | Responsive Insect Behavior |
|---|---|
| Geraniol | repellant (high dose) attractant (low dose) |
| Citronellal | repellant |
| butanone | attractant |
| Neem oil *Azadirachta indica* | repellant |
| diethyl methylbenzamide | attracants |
| ethyl hexanediol | attracants |

Just which receptor(s) is responsible for detecting these known modulators of insect behavior, the detection of which results in a known behavioral response was heretofore largely unknown. A determination of how these known modulators physiologically effectuate a change in the activities of the insect is a prerequisite for the design of bio-rational methods of insect control. This includes a knowledge of the response properties of the olfactory chemoreceptor neurons to such known modulators of insect behavior.

Insects have multiple specialized structures called "sensilla" on their bodies including antennae, maxillary palps, legs, wings. These sensilla range in length from approximately 20 to 1500 μm, have different shapes, and are covered with a cuticle which in the case of olfactory sensilla is perforated with a series of microscopic pores. Within the cuticular structure are at least one and often several chemoreceptor neurons whose dendrites or outer segments are bathed in an extracellular fluid termed the sensillum lymph.

Multiporous sensilla are likely found on insects representing all orders, including but not limited to the Diptera (flies and mosquitoes), Lepidoptera (moths and butterflies), Coleoptera (beetles), Hymenoptera (bees, wasps, ants), Siphonaptera (fleas), and Orthoptera (grasshoppers, cockroaches, crickets). Types of sensilla include sensilla basiconica which are found on the maxillary palps and antennae of mosquitoes, sensilla trichodea which are found on the antennae, sensilla coeloconica which are found on the antennae, and sensilla ampullacea which are found on the antennae.

Figure 1A:
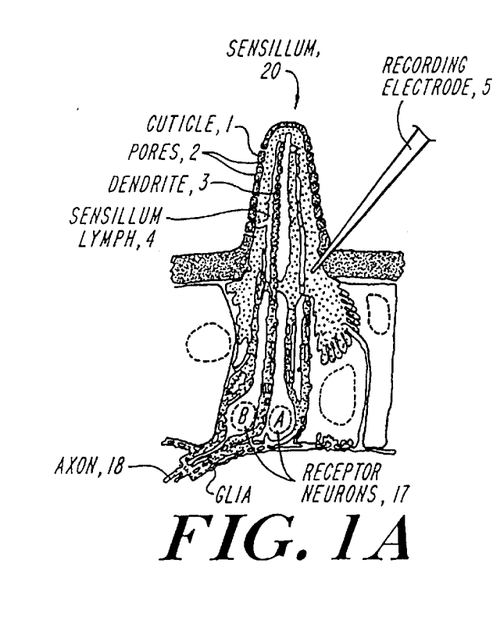
FIG. 1 is a diagrammatic representation of an insect sensillum and the set-up of the screening method of the invention.
Figure 1B:
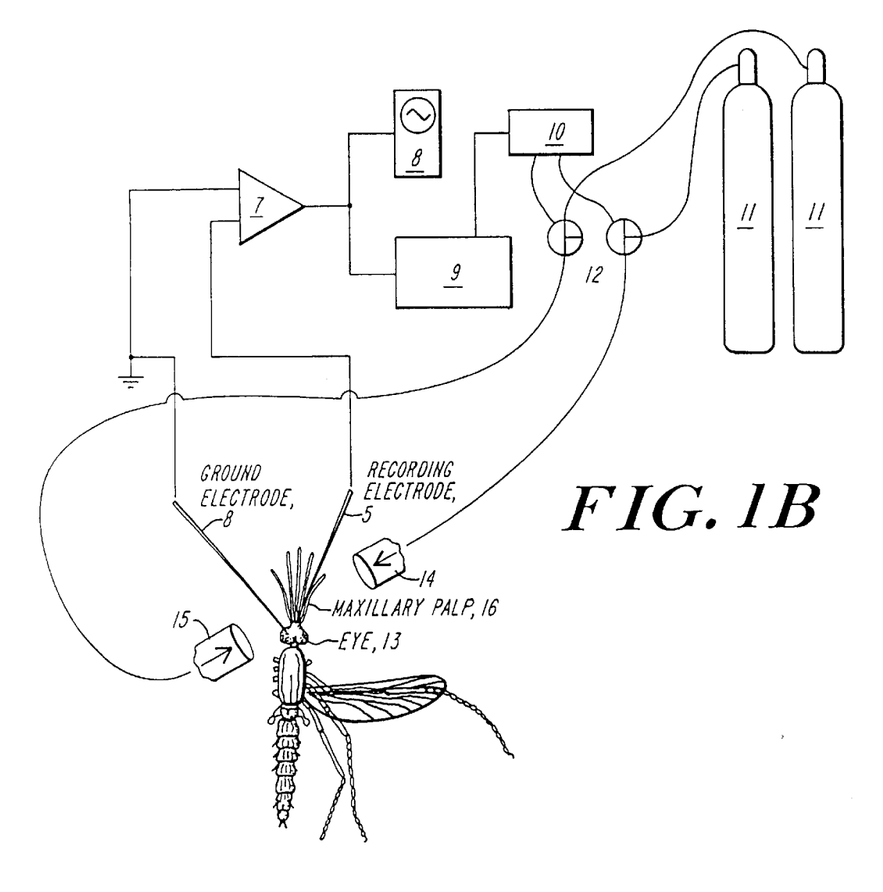

The sensilla basiconica, or palpal pegs or cones are shown diagrammatically in FIG. 1. These sensilla 20 are approximately 10 to 30 μm in length and may be enlarged distally to form a spoon-shaped structure whose cuticular surface is covered with pores 2. Sensilla basiconica on maxillary palps 16 of mosquitoes are innervated by three primary chemoreceptor neurons A, B, and C whose outer segments (dendrites) 3 are bathed in sensillum lymph 4. The axons 18 of these neurons 17 transmit information in the form of the rate and frequency spectrum of action potentials to the central nervous system of the animals.

One of these chemoreceptor neurons (neuron A) produces a large amplitude action potential and responds to stimulation with small amounts of carbon dioxide, a volatile stimulus thought to be involved with host seeking behavior (Daykin et al. (1965) *Canadian Entomol.* 97:239–263); Takken (1991) *Insect Sci. Applic.* 12:287–295). Carbon dioxide-sensitive chemoreceptor neurons are also found in the sensilla of other arthropods, including Lepidoptera, Hymenoptera, other Diptera, and Arachnida.

The other two primary chemoreceptor neurons found in the mosquito sensillum basiconicum (B and C) produce smaller amplitude action potentials and are spontaneously-active, but what stimulates them was heretofore unknown. However, using the method of the invention, it has been determined that other compounds known to modulate insect behavior, with the exception of carbon dioxide, are able to cause a response in at least one of the carbon dioxide-insensitive primary chemoreceptor cells in the sensilla at concentrations appropriate for a role in host seeking behavior. Thus, test compounds which stimulate at least one or another of these neurons are likely new behavioral modulators.

Likewise, according to the invention, neurons in other sensilla which are found to respond to other known modulators of insect behavior can be used to screen other test compounds which should cause the same type of behavioral and physiological response in the insect.

When a sensory receptor such as the chemoreceptor neuron discussed herein is stimulated, the receptor produces a change in an electrical characteristic. Thus, the neuroelectric response to stimuli can be monitored by measuring an electrical characteristic of the stimulated neuron. Useful measurable electrical characteristics include, for example, changes in the magnitude of the electrical potential, or in its frequency spectrum. The electrical activity of the stimulated neuron is preferably described in terms of a change in voltage (i.e., the electrical characteristic) called a generator potential, which initiates a sequence of events that leads to a propagating extracellular action potential measurable on an oscilloscope or other instrument. The voltage parameter corresponds to a difference in electrical potential between the chemoreceptor neuron of interest and a point remote from the neuron. The potential difference may be measured using an electrode arrangement in electrical contact with suitable anatomical regions of the subject insect.

The electrical potential, in particular, can be measured by inserting a recording electrode 5 through the cuticle 1 at the base of the sensillum 20 such that it is in electrical contact with the extracellular fluid or lymph 4 surrounding the chemoreceptor neurons within (FIG. 1). Useful electrodes are made of tungsten or another metal wire which has a sharpened microscopic tip. A second or ground electrode 6 is inserted into the insect at a position external to or remote from the sensillum being monitored. For example, the second electrode may be placed in an eye 13 or some other anatomical location (FIG. 1). Electrodes 5 and 6 are coupled to inputs of a differential amplifier 7. The amplifier 7 generates a signal representative of the difference in potential detected by electrodes 5 and 6. That signal is applied to an oscilloscope 8 (for visual display), and by way of a computer processing unit (CPU) monitoring system 9, to a digital input/output controller 10. In the illustrated embodiment, two gas tanks 11 are coupled by way of valves 12 to provide gas streams 14 and 15 directed towards the exposed palp 16. One of the tanks 11 provides background (e.g., synthetic gas, $CO_2$, or free air) and the other provides the stream to deliver the stimulus.

In operation, controller 10 controls valves 12 to direct the appropriate gas flow to the palp 16. Electrical signals represented by action potentials (i.e., voltage pulses of various amplitudes and shapes) from the neurons are amplified and forwarded to monitoring system 9 and microcomputer controller 10 for data acquisition, action potential discrimination, analysis, and storage. The discrimination function is an important component of the signal processing since the electrical activity of the stimulated sensillum includes a composite of the electrical responses from the whole set of chemoreceptor neurons within the sensillum. Accordingly, it may be necessary to resolve the entire electrical response into its constituent electrical components each representative of the response of a particular neuron.

Figure 6:
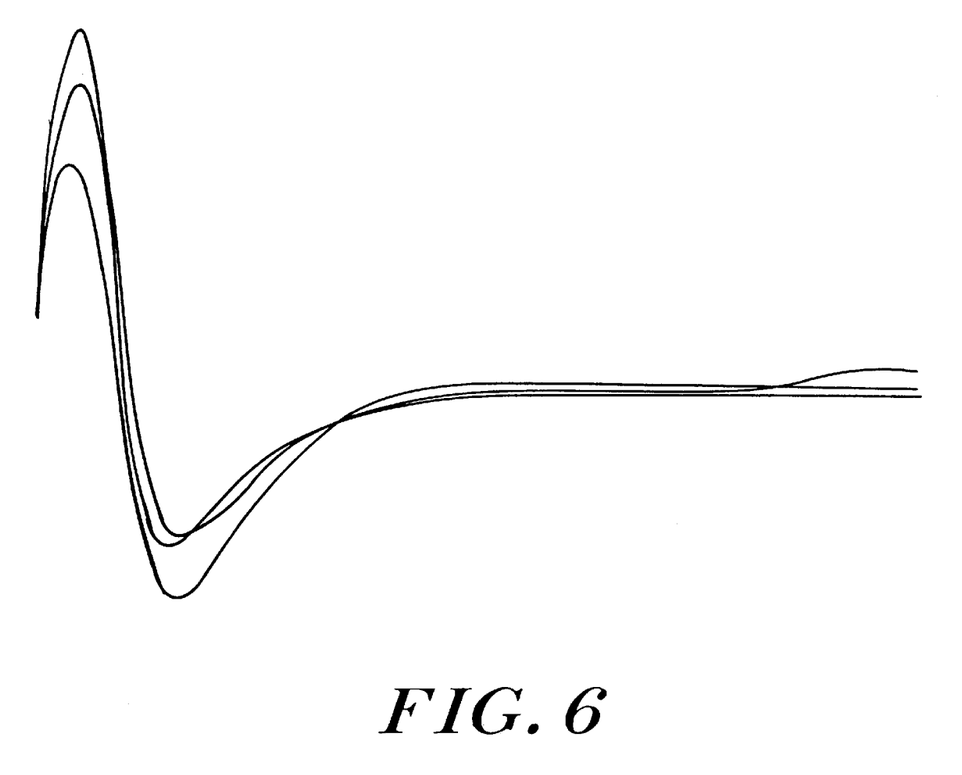
FIG. 6 is a waveform representation of action potentials recorded from one sensillum of an insect containing three chemoreceptor neurons.

It has been determined that the amplitudes and waveshapes of the action potentials produced by the three primary neurons in sensilla basiconica are different (e.g., see FIG. 6). The action potential amplitude of the mosquito carbon dioxide-responsive neuron A is larger (about 300 $\mu V$) than the amplitudes (about 50 to 100 $\mu V$) produced by the other two neurons. Consequently, discrimination between and resolution of the action potentials elicited from neuron A and those from neurons B and C is routinely possible.

In the past, however, discrimination or signal sorting between the two smaller amplitude action potentials was very difficult, if not impossible to accomplish. This is especially true of any sorting technique that relies solely on differences in action potential amplitude. However, the computer-based data acquisition and analysis techniques used herein make it possible to reliably discriminate between the activity of these receptor neurons by utilizing information about both the amplitude and the waveform of the action potentials they generate. This makes it possible to determine the nature of their firing upon stimulation, and the degree of spontaneous firing in the absence of a stimulus. The recording and analysis techniques employed greatly increase the ability to detect differences in the amplitude and shape of the action potentials recorded from these neurons, thus allowing the reliable identification and sorting of the responses of all three neurons in most recordings.

The following experiments evaluate both the static and dynamic response properties of the olfactory receptor neurons involved with detecting and processing the natural and synthetic volatile compounds known or suspected to be effective in modulating host-seeking behaviors.

Figure 2A:
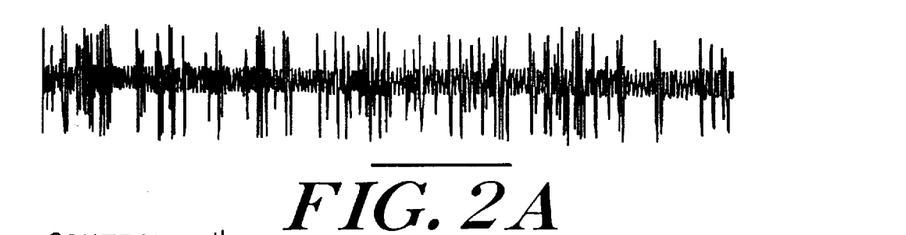
FIG. 2A is a trace showing the electrical activity recorded from a single sensillum basiconicum during stimulation with a control, wherein the bar under each record indicates the timing and duration of the 2 second stimulus pulse.

In order to determine what, if any, electrophysiological response(s) are triggered by one or both of the carbon dioxide-insensitive neurons (B and C), a single mosquito sensillum basiconicum was contacted with 1-octen-3-ol, a known single component behavioral "attractant" (see, e.g., Otter et al. (1988) *Insect Sci. Applic.* 9:213–318; Kline et al. (1990) *Med. Veter. Entomol.* 4:383–391; Kline et al. (1991) *J. Med. Entomol.* 28:254–258). Increasing doses of 1-octen-3-ol diluted in hexane (0.0001 to 0.01 $\mu g/\mu l$) were delivered in a synthetic air stream containing 0 ppm carbon dioxide. FIGS. 2A–2D illustrate the electrophysiological responses elicited in the neurons of the sensillum in response to this stimulus. The dose indicated under each trace represents the amount of material applied to the stimulus cartridge and not the amount actually delivered to the insect. These results demonstrate that neuron C producing the smallest amplitude action potential is very sensitive and responds in a dose-dependent manner to this material. No response was observed in neuron B which produces the medium amplitude potential, or in neuron A which is normally responsive to $CO_2$. None of the receptor neurons were responsive to stimulation with an odor cartridge containing the hexane diluent (control) alone (FIG. 2A). FIG. 3 plots the dose response functions of each of the three neurons in this single sensillum. This figure demonstrates that neuron C is responsive to 1-octen-3-ol even at doses as low as $1\times10^{-5}$ $\mu g$, while the other two neurons, A and B, are not responsive to elevated doses as high as $1\times10^{-1}$.

Figure 2B:
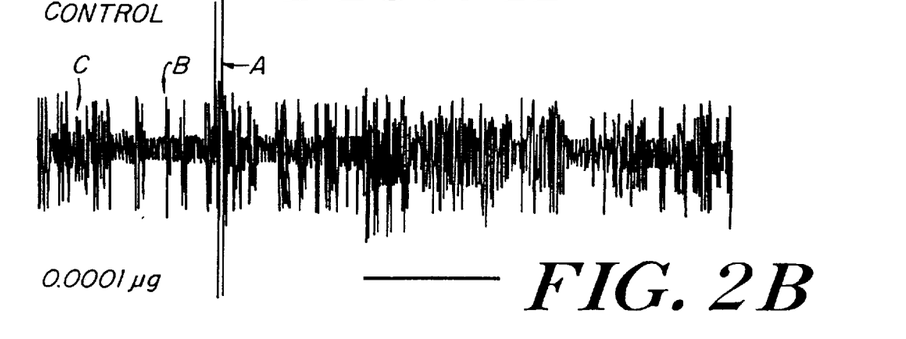
FIG. 2B is a trace showing the response of the A, B, and C neurons in the same sensillum to a $1 \times 10^{-4}$ μg dose of 1-octen-3-ol, wherein labels have been included to mark examples of the action potentials from each of the three receptor neurons.
Figure 2C:
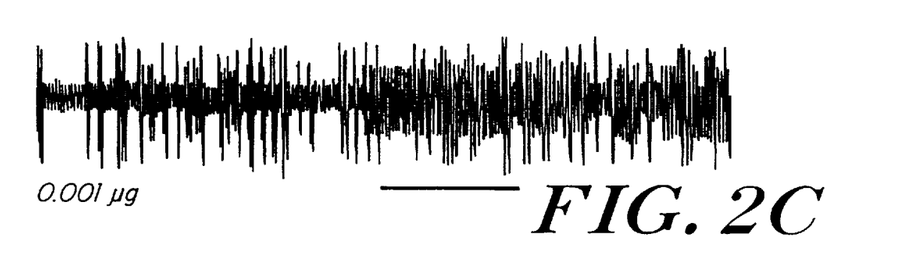
FIG. 2C is a trace showing the response of the A, B, and C neurons in the same sensillum to a $1 \times 10^{-3}$ μg dose of 1-octen-3-ol.
Figure 2D:
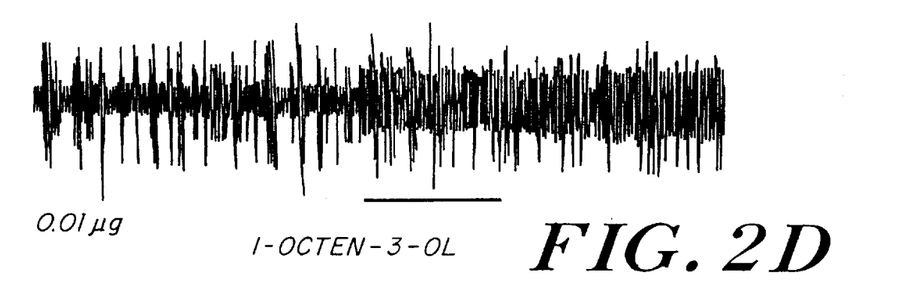
FIG. 2D is a trace showing the response of the A, B, and C neurons in the same sensillum to a $1 \times 10^{-2}$ g dose of 1-octen-3-ol.
Figure 3:
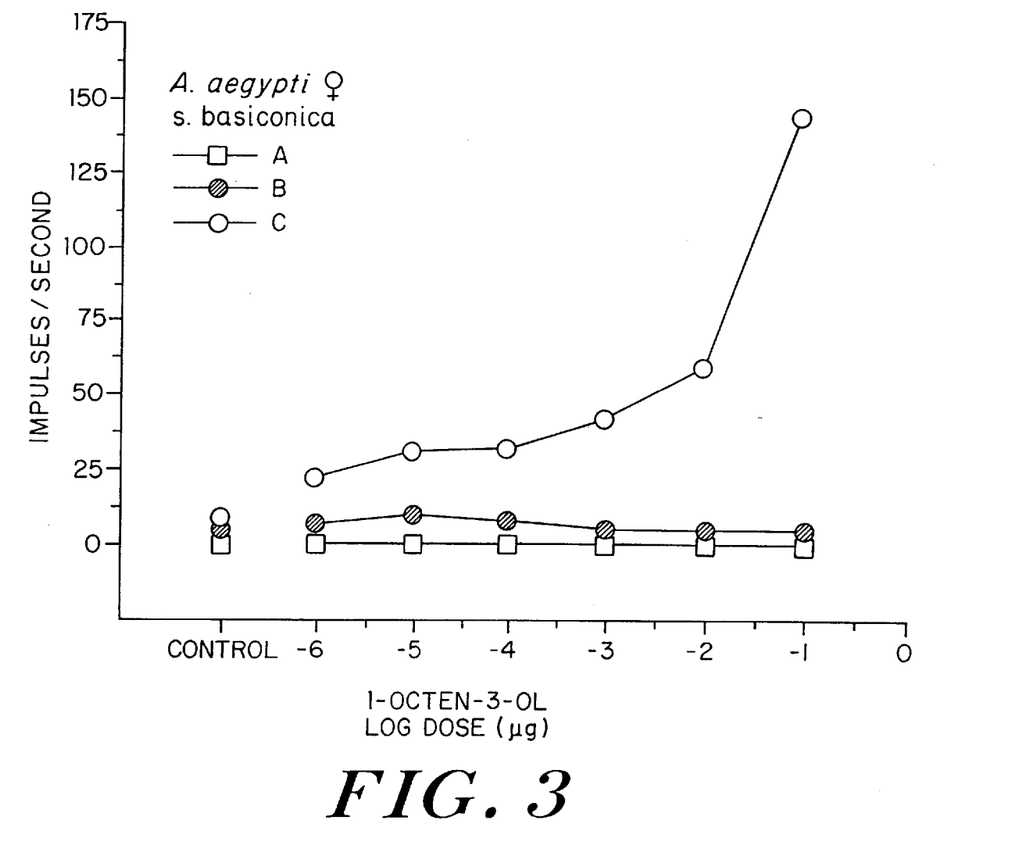
FIG. 3 is a graphic representation of the dose response functions for graded doses of 1-octen-3-ol from the A (□), B (●), and C (○) receptor neurons in the same sensillum basiconicum as FIGS. 2A–2D.

The results shown in FIGS. 2A–2D also demonstrate the degree of separation that can be achieved between the action potentials of the three neurons in this sensillum. In these recordings, the gain of the amplifier was adjusted so that the potentials from the carbon dioxide-sensitive chemoreceptor neuron (A) is offscale (FIG. 2B). A brief (200 msec) pulse of $CO_2$ was delivered two seconds before the stimulus in 2B to identify the neuron. The spontaneous discharge rates of the neurons B and C producing the smaller amplitude action potentials range, on average, from 5 to 15 impulses in a background containing 0 ppm carbon dioxide (FIG. 2A). Recordings of this type have been observed for many mosquito species tested, such as *Aedes aegypti, Anopheles stephensi*, and *Culex quinquefaciatus*.

Figure 4:
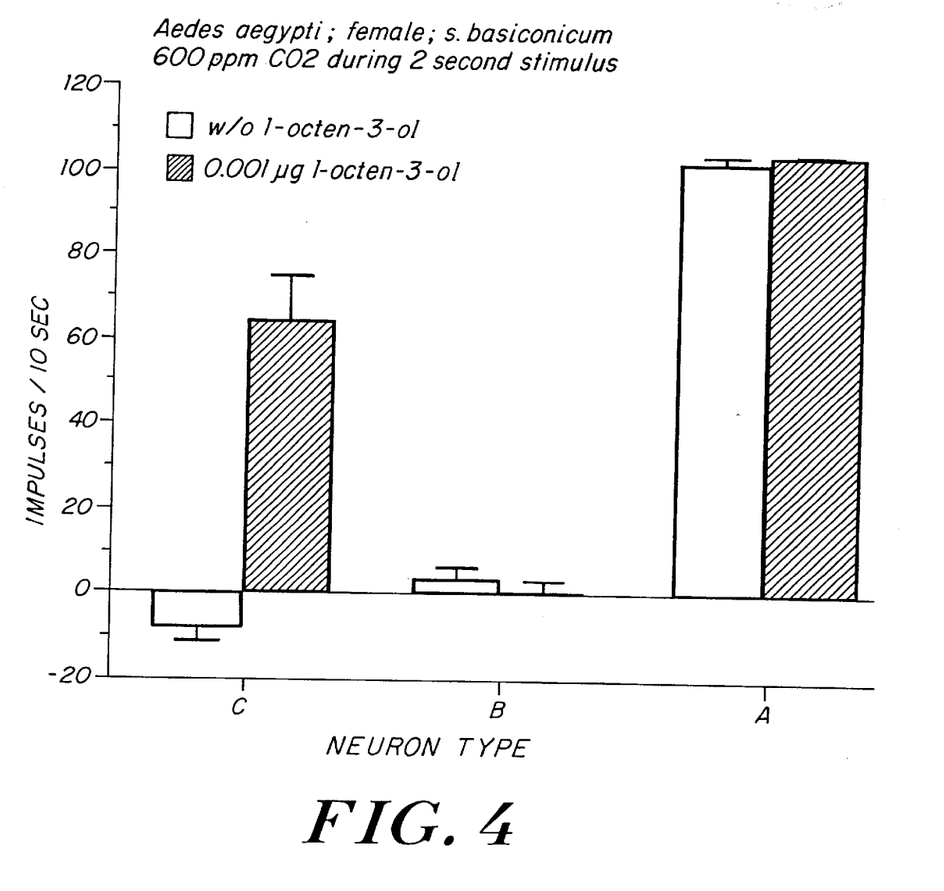
FIG. 4 is a graphic representation illustrating the response, averaged over three presentations, of the A, B, and C neurons in the same sensillum basiconicum tested in FIGS. 2A–2D and 3 to a stimulus containing 600 ppm of $CO_2$ with (■), or without (□) the addition of 0.001 μg of 1-octen-3-ol to the stimulus.

To determine whether the B and C neurons producing the smaller amplitude action potentials respond to stimulation with carbon dioxide, the neurons in the same sensillum basiconicum tested in FIGS. 2A–D and 3 were stimulated with $CO_2$ and 1-octen-3-ol. FIG. 4 illustrates the responses from all three cells to a stimulus pulse of 600 ppm $CO_2$ alone (—□—), and to a stimulus pulse of 600 ppm $CO_2$ plus 0.001 g 1-octen-3-ol (—■—). The responses depicted in this graph are expressed as ΔR, or the change in response during and immediately following the stimulus. This measure was calculated by subtracting the first 10 seconds of pre-stimulus impulse activity from the subsequent 10 seconds of stimulus and post-stimulus activity. Such a response measure is often used when neurons have spontaneous impulse activity. Again, as expected, the A neuron responds to $CO_2$ and the C neuron responds to 1-octen-3-ol. In contrast, the B neuron does not respond to either substance. In summary, (1) the A cell responds to $CO_2$ but not 1-octen-3-ol; (2) the B cell does not respond to either $CO_2$ or 1-octen-3-ol; (3) the C cell does not respond to $CO_2$, but does respond to 1-octen-3-ol; and (4) that the presence of 1-octen-3-ol does not alter the A cell's response to $CO_2$.

Figure 5A:
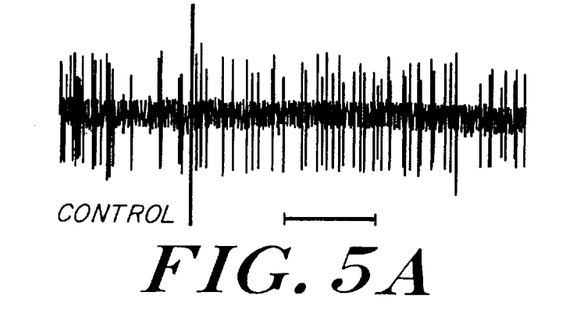
FIG. 5A is a trace showing the response elicited in the three receptor neurons found in another sensillum basiconicum by a control stimulus. Conventions the same as in FIGS. 2A–2D.
Figure 5B:
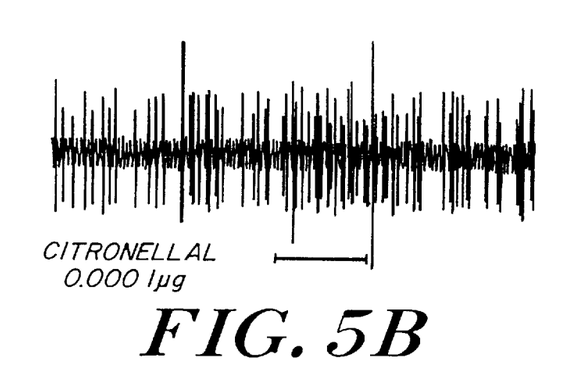
FIG. 5B is a trace showing the response of the A, B, and C neurons in the same sensillum to a $1\times10^{-4}$ μg dose of citronellal.
Figure 5C:
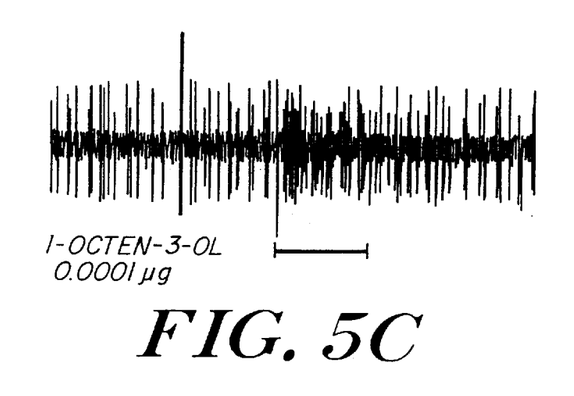
FIG. 5C is a trace showing the response of the A, B, and C neurons in the same sensillum to a $1\times10^{-4}$ dose of 1-octen-3-ol.

To determine whether any of these sensilla neurons are responsive to a known insect repellant, a commercial sample of citronellal (3,7-dimethyl-6-octenal) was administered to another sensillum (FIG. 5B). Citronellal is regarded as a behaviorally active material (Davis (1985) *J. Med. Entomol.* 22:237–243). As shown in FIG. 5B, citronellal elicits activity from the same neuron (C) that responds to 1-octen-3-ol (FIG. 5C). The recordings in this figure suggest that neuron C is somewhat less sensitive to citronellal. The amplifier gain has again been adjusted so that the action potentials from the carbon dioxide receptor neuron are off-scale. In this figure, a brief (200 millisec) exposure to ambient levels of carbon dioxide (about 300 ppm) was triggered 2 seconds before the pulse (marked by the bar under each record) to insure that activity from all 3 neurons are present in the recordings, (recalling that carbon dioxide receptors are silent in 0 ppm carbon dioxide).

Collectively these experiments demonstrate that the sensilla basiconica on the maxillary palps of mosquitoes contain highly sensitive olfactory receptor neurons, at least one of which (neuron C) responds to known insect repellants and attractants.

The following examples illustrate the preferred modes of making and practicing the present invention, but are not meant to limit the scope of the invention since alternative methods may be utilized to obtain similar results.

EXAMPLES

1. Insects

*Aedes aegypti* (Rockefeller Institute, NY, N.Y.; and University of Massachusetts, Amherst, Mass.), *Anopheles stephensi* (Walter Reed, Baltimore, Md., *Culiseta melanura* (University of Massachusetts, Amherst, Mass., as larvae), *Culex quinquefaciatus, Culiseta melanura* and *Aedes taeniorhynchus* (from USDA, Gainesville, Fla. as eggs; Vero Beach strain) stocks were raised in the insectary at American Biophysics, Jamestown, R.I. under a 12:12 (L:D) hour photoperiod at approximate 21°–27° C. and 62–64% RH and were given 10% sucrose ad lib as adults. Larvae were fed either ground dry dog biscuits or ground tropical fish food.

2. Recording

Standard electrophysiological techniques as described by O'Connell (*J. Gen. Physiol.* (1975) 65:179–205), and Grant et al. (*J. Insect Physiol.* (1986) 32:503–515; *J. Insect Behav.* (1989) 3:371–385) were used to record extracellular responses from the receptor neurons housed in the sensilla basiconica on the maxillary palps of mosquito. Briefly, mosquitoes were immobilized on a microscope stage with adhesive ("Tanglefoot") and double-sided tape. A tungsten recording micro-electrode was inserted at the sensillum base and an indifferent electrode was placed in the eye (FIG. 1). The electrical signals (i.e., voltage amplitudes) obtained from the neurons are bandpass filtered, amplified, and sent in parallel to an audio monitor, a storage oscilloscope, and a microcomputer for data acquisition, action potential discrimination and analysis, and storage. The computerized data collection and analysis system employs digitization apparatus performing analog to digital conversion for digitally sampling the collected voltage amplitudes. The digitized voltage samples, which correspond to a digital representation of the nerve impulses, are stored in memory and define the electrical response to a single stimulus presentation. The microcomputer is operative to access the digitized samples in storage for sorting the electrical activity generated by all receptor neurons in a sensillum.

The classification of the action potentials is achieved by computing a statistic from each set of voltage samples defining an individual action potential. Once scaled, this statistic (the standard deviation, SD) is influenced by both the amplitude and waveform of the action potential. By operation of an analysis program, the histograms of standard deviation are organized into a distribution profile in which each mode of the distribution represents action potentials from a particular receptor. Thus, by partitioning the distribution into its component modes, the electrical activity generated by the stimulated sensillum is resolved into individually distinguishable neuroresponses, enabling accurate identification of the activity of each. The original nerve impulses (i.e., voltage amplitudes) may be reconstructed from the digitized voltage samples using a digital-to-analog converter, and then displayed as a waveform, with each reconstructed action potential trace being correlated with one of the neurons based on the SD sorting results. Recordings may be obtained from adult animals up to 28 days after emergence.

3. Stimulation

Two opposed gas streams were directed toward the exposed palp, one carrying the background (225 mls/min) and the other carrying or delivering stimulus (150 mls/min). Computer-activated valves controlled these streams and the delivery of $CO_2$ or the compound to be tested to the preparation, either from gas cylinders, each containing metered amounts of $CO_2$, or odor cartridges containing metered amounts of citronellal (FARCHAN Chemical Corp., Willoughly, Ohio) or 1-octen-3-ol (Aldrich Chemical Co., Milwaukee, Wis.) as described in O'Connell (*J. Gen. Physiol.* (1975) 65:179–205), Grant and O'Connell (*J. Insect. Physiol.* (1986) 32:503–515), or Grant et al. (*J. Insect. Behav.* (1989) 3:371–385).

Increasing doses of 1-octen-3-ol or other single or multi-component compounds to be tested diluted in hexane (0.0001 to 0.01 $\mu g/\mu l$) or some other non-stimulus diluent were delivered from an odor cartridge with a synthetic air stream containing 0 ppm carbon dioxide.

To establish the concentration response relationship, the sensillum was then stimulated with successive two second pulses of each of the concentrations of compound to be evaluated. To insure that the stimulus pulses were as rectangular as possible, the stimulus line was activated four seconds before the opposed background stream was shut off to produce the two second stimulus pulse. During the four second pre-pulse interval, the elevated flowrate in the background stream prevented the stimulus stream from reaching the preparation. This was readily verified, in each case, by the constancy of the receptor neuron activity during the pre-pulse period. This method of delivery insures that the flow stimulus is equilibrated and constant during the entire stimulus pulse and greatly reduces that component of the response latency that is due to stimulus delivery to the preparation (Borroni et al. (1992) *J. Comp. Physiol. A.* 170:691–700)

The difference in flow rate between the two gas streams did not effect the response of the receptor neuron. Responses, unless otherwise noted, are expressed as the total number of action potentials elicited during the two-second pulse. Each stimulus pulse was separated by a 2 to 3 minute return to the background level. The order of presentation of both control and stimulus concentration was randomly determined.

4. Behavioral Testing

The behavioral response of mosquitoes to the compound being tested is monitored with a wind tunnel system equipped with direct observation and video techniques essentially as described by Eiras et al. (*Bull. Entomol. Res.* (1991) 81:151–150). Briefly, three hour-starved mosquitoes are placed in a release tube fixed inside the tunnel and released. The wind tunnel is a plastic tube 1.3 m long, with a diameter of 38 cm. inflated by two electric fans. The video system consists of a Panisonic WV-1850 camera mounted vertically, and a Hitachi VT-L30ED time-lapse video recorder. The wind tunnel is maintained at 27° C. and 60% relative humidity. The behavioral responses of the test insects (e.g., takeoff, probing activity, flight activity, and landing behavior) are monitored over seven minutes. In the first two minutes, no stimulus was present. During the next five minutes, full exposure to the stimulus occurs. The stimulus is placed in a cylindrical, cotton glass pipette filter which is placed in a glass vial containing the test compound. A small flow chamber releases carbon dioxide or air at a controlled rate through a lid in which the vial is placed. The source is placed 20 cm above the tunnel floor. The gaseous flow rate (about 500 ml/min) is matched to the wind speed within the tunnel. A human observer records events at one minute intervals, and the video system records events continuously.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method of selecting for a compound which modulates the behavior of an insect, comprising the steps of:
   (a) measuring an electrical characteristic of a chemoreceptor neuron in a sensillum of the insect in the presence of control stimulation to determine a measure of baseline activity (A) for the neuron;
   (b) contacting the neuron during a stimulation period with a known chemical modulator of the behavior of the insect;
   (c) measuring an electrical characteristic produced by the neuron in response to the contacting with the known modulator to determine a measure of known modulator-induced activity (C) for the neuron, wherein C is representative of a correlation between the neuron and the modulator-induced behavior of the insect;
   (d) contacting the neuron with a compound-to-be-tested;
   (e) measuring an electrical characteristic produced by the contacted neuron in response to the contacting with the compound to determine a measure of unknown modulator-induced activity (E) of the neuron;
   (f) comparing A, C, and E; and
   (g) when C is greater than A, classifying, based on the comparison of step (f), the compound with respect to its ability to modulate the behavior of the insect.

2. The method of claim 1 wherein the electrical characteristics are varying frequency successions of voltage pulses produced by the neuron.

3. The method of claim 2 wherein A is representative of the number of pulses produced by the neuron in step (a) during a period corresponding to the stimulation period, C is the number of pulses produced by the neuron during the stimulation period in step (c), and E is the number of pulses produced by the neuron during a period corresponding to the stimulation period in step (e).

4. The method of claim 2 wherein A is representative of the peak instantaneous repetition rate of the pulses produced by the neuron in step (a) during a period corresponding to the stimulation period, C is the peak instantaneous repetition rate of the pulses produced by the neuron in step (c) during the stimulation period, and E is the peak instantaneous repetition rate of the number of pulses produced by the neuron in step (e) during a period corresponding to the stimulation period.

5. The method of claim 2 wherein C is representative of the third moment of the distribution of interpulse periods of the succession of pulses produced by the neuron in step (c) during the stimulation period, and E is representative of the third moment of the distribution of interpulse period of the secession of pulses produced by the neuron in step (e) during a period corresponding to the stimulation period, whereby C or E each are in a range from −1 to +1 on the real number line, and wherein a first value of C or E is greater than a second value of C or E, respectively, if the first value is closer to −1 than is the second value.

6. The method of claim 2 wherein:
   (i) A is representative of the mean instantaneous pulse repetition rate during step (a);
   (ii) the succession of pulses produced by the neuron in step (c) is characterized by an initial phasic component followed by a tonic component during the stimulation period, wherein during the phasic component, a relatively large number of pulses per unit time are produced by the neuron and during the tonic component, a relatively small number of pulses are produced by the neuron per unit time, and wherein $C_T$ is representative of the mean instantaneous pulse repetition rate during the tonic component and $C_P$ is representative of the peak instantaneous pulse repetition rate during the phasic component, and wherein $C_P^2/C_T$ corresponds to C; and (iii) the succession of pulses produced by the neuron in step (e) is characterized by an initial phasic component followed by a tonic component during a period corresponding to the stimulation period, wherein during the phasic component, a relatively large number of pulses per unit time are produced by the neuron and during the tonic component, a relatively small number of pulses are produced by the neuron per unit time, and wherein $E_T$ is representative of the mean instantaneous pulse repetition rate during the tonic component and $E_P$ is representative of the peak instantaneous pulse repetition rate during the phasic component, and wherein $E_P^2/E_T$ corresponds to E.

7. The method of claim 1 wherein E=C, and wherein classifying step (g) classifies the compound as having potency substantially equal to the known modulator.

8. The method of claim 7 wherein the electrical characteristics are varying frequency successions of voltage pulses produced by the neuron.

9. The method of claim 8 wherein A is representative of the number of pulses produced by the neuron in step (a) during a period corresponding to the stimulation period, C is the number of pulses produced by the neuron during the stimulation period in step (c), and E is the number of pulses produced by the neuron during a period corresponding to the stimulation period in step (e).

10. The method of claim 8 wherein A is representative of the peak instantaneous repetition rate of the pulses produced by the neuron in step (a) during a period corresponding to the stimulation period, C is the peak instantaneous repetition rate of the pulses produced by the neuron in step (c) during the stimulation period, and E is the peak instantaneous repetition rate of the number of pulses produced by the neuron in step (e) during a period corresponding to the stimulation period.

11. The method of claim 8 wherein C is representative of the third moment of the distribution of interpulse periods of the succession of pulses produced by the neuron in step (c) during the stimulation period, and E is representative of the third moment of the distribution of interpulse period of the secession of pulses produced by the neuron in step (e) during a period corresponding to the stimulation period, whereby C and E each are in a range from −1 to +1 on the real number line, and wherein a first value of C or E is greater than a second value of C or E, respectively if the first value is closer to −1 than is the second value.

12. The method of claim 8 wherein:

(i) A is representative of the mean instantaneous pulse repetition rate during step (a);

(ii) the succession of pulses produced by the neuron in step (c) is characterized by an initial phasic component followed by a tonic component during the stimulation period, wherein during the phasic component, a relatively large number of pulses per unit time are produced by the neuron and during the tonic component, a relatively small number of pulses are produced by the neuron per unit time, and wherein $C_T$ is representative of the mean instantaneous pulse repetition rate during the tonic component and $C_P$ is representative of the peak instantaneous pulse repetition rate during the phasic component, and wherein $C_P^2/C_T$ corresponds to C; and (iii) the succession of pulses produced by the neuron in step (e) is characterized by an initial phasic component followed by a tonic component during a period corresponding to the stimulation period, wherein during the phasic component, a relatively large number of pulses per unit time are produced by the neuron and during the tonic component, a relatively small number of pulses are produced by the neuron per unit time, and wherein $E_T$ is representative of the mean instantaneous pulse repetition rate during the tonic component and $E_P$ is representative of the peak instantaneous pulse repetition rate during the phasic component, and wherein $E_P^2/E_T$ corresponds to E.

13. The method of claim 1 wherein E is greater than C, and wherein classifying step (g) classifies the compound as having greater potency than the known modulator.

14. The method of claim 13 wherein the electrical characteristics are varying frequency successions of voltage pulses produced by the neuron.

15. The method of claim 14 wherein A is representative of the number of pulses produced by the neuron in step (a) during a period corresponding to the stimulation period, C is the number of pulses produced by the neuron during the stimulation period in step (c), and E is the number of pulses produced by the neuron during a period corresponding to the stimulation period in step (e).

16. The method of claim 14 wherein A is representative of the peak instantaneous repetition rate of the pulses produced by the neuron in step (a) during a period corresponding to the stimulation period, C is the peak instantaneous repetition rate of the pulses produced by the neuron in step (c) during the stimulation period, and E is the peak instantaneous repetition rate of the number of pulses produced by the neuron in step (e) during a period corresponding to the stimulation period.

17. The method of claim 14 wherein C is representative of the third moment of the distribution of interpulse periods of the succession of pulses produced by the neuron in step (c) during the stimulation period, and E is representative of the third moment of the distribution of interpulse period of the secession of pulses produced by the neuron in step (e) during a period corresponding to the stimulation period, whereby C and E each are in a range from −1 to +1 on the real number line, and wherein a first value of C or E is greater than a second value of C or E, respectively, if the first value is closer to −1 than is the second value.

18. The method of claim 14 wherein:

(i) A is representative of the mean instantaneous pulse repetition rate during step (a);

(ii) the succession of pulses produced by the neuron in step (c) is characterized by an initial phasic component followed by a tonic component during the stimulation period, wherein during the phasic component, a relatively large number of pulses per unit time are produced by the neuron and during the tonic component, a relatively small number of pulses are produced by the neuron per unit time, and wherein $C_T$ is representative of the mean instantaneous pulse repetition rate during the tonic component and $C_P$ is representative of the peak instantaneous pulse repetition rate during the phasic component, and wherein $C_P^2/C_T$ corresponds to C; and (iii) the succession of pulses produced by the neuron in step (e) is characterized by an initial phasic component followed by a tonic component during a period corresponding to the stimulation period, wherein during the phasic component, a relatively large number of pulses per unit time are produced by the neuron and during the tonic component, a relatively small number of pulses are produced by the neuron per unit time, and wherein $E_T$ is representative of the mean instantaneous pulse repetition rate during the tonic component and $E_P$ is representative of the peak instantaneous pulse repetition rate during the phasic component, and wherein $E_P^2/E_T$ corresponds to E.

19. The method of claim 1 wherein E is less than C, and E is greater than A, and wherein classifying step (g) classifies the compound as having lesser potency than the known modulator.

20. The method of claim 19 wherein the electrical characteristics are varying frequency successions of voltage pulses produced by the neuron.

21. The method of claim 20 wherein A is representative of the number of pulses produced by the neuron in step (a) during a period corresponding to the stimulation period, C is the number of pulses produced by the neuron during the stimulation period in step (c), and E is the number of pulses produced by the neuron during a period corresponding to the stimulation period in step (e).

22. The method of claim 20 wherein A is representative of the peak instantaneous repetition rate of the pulses produced by the neuron in step (a) during a period corresponding to the stimulation period, C is the peak instantaneous repetition rate of the pulses produced by the neuron in step (c) during the stimulation period, and E is the peak instantaneous repetition rate of the number of pulses produced by the neuron in step (e) during a period corresponding to the stimulation period.

23. The method of claim 20 wherein C is representative of the third moment of the distribution of interpulse periods of the succession of pulses produced by the neuron in step (c) during the stimulation period, and E is representative of the third moment of the distribution of interpulse period of the secession of pulses produced by the neuron in step (e) during a period corresponding to the stimulation period, whereby C and E each are in a range from −1 to +1 on the real number line, and wherein a first value of C or E is greater than a second value of C or E if the first value is closer to −1 than is the second value.

24. The method of claim 20 wherein:
(i) A is representative of the mean step (a);
(ii) the succession of pulses produced by the neuron in step (c) is characterized by an initial phasic component followed by a tonic component during the stimulation period, wherein during the phasic component, a relatively large number of pulses per unit time are produced by the neuron and during the tonic component, a relatively small number of pulses are produced by the neuron per unit time, and wherein $C_T$ is representative of the mean instantaneous pulse repetition rate during the tonic component and $C_P$ is representative of the peak instantaneous pulse repetition rate during the phasic component, wherein $C_P^2/C_T$ corresponds to C; and
(iii) the succession of pulses produced by the neuron in step (e) is characterized by an initial phasic component followed by a tonic component during a period corresponding to the stimulation period, wherein during the phasic component, a relatively large number of pulses per unit time are produced by the neuron and during the tonic component, a relatively small number of pulses are produced by the neuron per unit time, and wherein $E_T$ is representative of the mean instantaneous pulse repetition rate during the tonic component and $E_P$ is representative of the peak instantaneous pulse repetition rate during the phasic component, and wherein $E_P^2/E_T$ corresponds to E.

25. The method of claim 1 wherein E is less than A, and wherein classifying step (g) classifies the compound as being an inhibitor of the behavior modulated by the known modulator.

26. The method of claim 25 wherein the electrical characteristics are varying frequency successions of voltage pulses produced by the neuron.

27. The method of claim 26 wherein A is representative of the number of pulses produced by the neuron in step (a) during a period corresponding to the stimulation period, C is the number of pulses produced by the neuron during the stimulation period in step (c), and E is the number of pulses produced by the neuron during a period corresponding to the stimulation period in step (e).

28. The method of claim 26 wherein A is representative of the peak instantaneous repetition rate of the pulses produced by the neuron in step (a) during a period corresponding to the stimulation period, C is the peak instantaneous repetition rate of the pulses produced by the neuron in step (c) during the stimulation period, and E is the peak instantaneous repetition rate of the number of pulses produced by the neuron in step (e) during a period corresponding to the stimulation period.

29. The method of claim 26 wherein A is representative of the third moment of the distribution of interpulse periods of the succession of pulses produced by the neuron in step (a) during a period corresponding to the stimulation period, C is representative of the third moment of the distribution of interpulse periods of the succession of pulses produced by the neuron in step (c) during the stimulation period, and E is representative of the third moment of the distribution of interpulse period of the secession of pulses produced by the neuron in step (e) during a period corresponding to the stimulation period, whereby A, C, and E each are in a range from −1 to +1 on the real number line, and wherein a first value of A, C, and E is greater than a second value of A, C, and E if the first value is closer to −1 than is the second value.

30. The method of claim 26 wherein:
(i) A is representative of the mean instantaneous pulse repetition rate during step (a);
(ii) the succession of pulses produced by the neuron in step (c) is characterized by an initial phasic component followed by a tonic component during the stimulation period, wherein during the phasic component, a relatively large number of pulses per unit time are produced by the neuron and during the tonic component, a relatively small number of pulses are produced by the neuron per unit time, and wherein $C_T$ is representative of the mean instantaneous pulse repetition rate during the tonic component and $C_P$ is representative of the peak instantaneous pulse repetition rate during the phasic component, wherein $C_P^2/C_T$ corresponds to C; and
(iii) the succession of pulses produced by the neuron in step (e) is characterized by an initial phasic component followed by a tonic component during a period corresponding to the stimulation period, wherein during the phasic component, a relatively large number of pulses per unit time are produced by the neuron and during the tonic component, a relatively small number of pulses are produced by the neuron per unit time, and wherein $E_T$ is representative of the mean instantaneous pulse repetition rate during the tonic component and $E_P$ is representative of the peak instantaneous pulse repetition rate during the phasic component, and wherein $E_P^2/E_T$ corresponds to E.

31. The method of claim 1 wherein the chemoreceptor neurons contacted are carbon dioxide-insensitive.

32. The method of claim 1 wherein the contacting step comprises contacting the neuron with a mixture of more than one compounds-to-be tested.

33. The method of claim 1 wherein the contacting step comprises directing a volatile form of the compound-to-be-tested toward the sensillum.

34. The method of claim 1 wherein the electrical characteristic measured is potential difference, and wherein each of the measuring steps comprises:
   (i) inserting a recording electrode into the base of the sensillum, whereby the first electrode is electrically coupled to the neuron;
   (ii) inserting a second electrode into an interior region of the insect remote from the sensillum; and
   (iii) measuring the difference in electrical potential between the first and second electrodes.

35. The method of claim 1 wherein the neuron is in a multiporous sensillum selected from the group consisting of sensilla basiconica, sensilla trichodea, sensilla coeloconica, and sensilla ampullacea.

36. The method of claim 35 wherein the neuron is in a sensillum basiconicum.

37. The method of claim 1 wherein the insect behavior sought to be modulated is selected from the group consisting of host-seeking behavior and mate-seeking behavior.

38. The method of claim 1 wherein the neuron contacted is in a sensilla on an insect selected from the group consisting of Diptera, Lepidoptera, Coleoptera, Hymenoptera, Siphonaptera, and Orthoptera.

39. The method of claim 1 wherein the electrical characteristic of a first neuron and the electrical characteristic of at least a second neuron are measured and resolved such that the characteristic of the first neuron is distinguishable from the characteristic of the second neuron.

40. The method of claim 39 wherein the first and second chemoreceptor neurons are mosquito sensilla basiconica carbon dioxide-insensitive neurons B and C.

* * * * *